United States Patent
Arenson et al.

(10) Patent No.: US 7,260,172 B2
(45) Date of Patent: Aug. 21, 2007

(54) METHOD AND SYSTEM OF CT DATA CORRECTION

(75) Inventors: Jerome Stephen Arenson, Haifa (IL); Evgeny Drapkin, Delafield, WI (US); Yanfeng Du, Rexford, NY (US); Lev Greenberg, Haifa (IL); Oded Meirav, Haifa (IL); David Ruimi, Netanya (IL); John Eric Tkaczyk, Delanson, NY (US); Xiaoye Wu, Rexford, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/627,072

(22) Filed: Jan. 25, 2007

(65) Prior Publication Data

US 2007/0116173 A1    May 24, 2007

Related U.S. Application Data

(62) Division of application No. 10/904,736, filed on Nov. 24, 2004.

(51) Int. Cl.
*G01N 23/083* (2006.01)

(52) U.S. Cl. .............................. 378/18; 378/4; 378/207

(58) Field of Classification Search .................... 378/4, 378/8, 16, 18, 20, 207, 901
See application file for complete search history.

(56) References Cited

U.S. PATENT DOCUMENTS 5,165,100 A    11/1992    Hsieh et al.
5,225,980 A *  7/1993    Hsieh et al. .................... 378/18
5,400,378 A *  3/1995    Toth ............................... 378/16
2004/0136491 A1    7/2004    Iatrou et al.
2004/0264627 A1    12/2004    Besson

OTHER PUBLICATIONS

F. Rashid-Farrokhi et al., "Local Tomography in Fan-Beam Geometry Using Wavelets," IEEE 1996, pp. 709-712.

* cited by examiner

*Primary Examiner*—Hoon Song
(74) *Attorney, Agent, or Firm*—Ziolkowski Patent Solutions Group, SC

(57) ABSTRACT

An adaptive CT data acquisition system and technique is presented whereby radiation emitted for CT data acquisition is dynamically controlled to limit exposure to those detectors of a CT detector assembly that may be particularly susceptible to saturation during a given data acquisition. The data acquisition technique recognizes that for a given subject size and position that pre-subject filtering and collimating of a radiation beam may be insufficient to completely prevent detector saturation. Therefore, the present invention includes implementation of a number of CT data correction techniques for correcting otherwise unusable data of a saturated CT detector. These data correction techniques include a nearest neighbor correction, off-centered phantom correction, off-centered synthetic data correction, scout data correction, planar radiogram correction, and a number of others. The invention is applicable with energy discriminating CT systems as well as with conventional CT systems and other multi-energy CT systems, such as dual kVp-based systems.

20 Claims, 9 Drawing Sheets

METHOD AND SYSTEM OF CT DATA CORRECTION

CROSS-REFERENCE TO RELATED APPLICATION

The present application is a divisional of and claims priority of U.S. Ser. No. 10/904,736 filed Nov. 24, 2004, the disclosure of which is incorporated herein by reference.

BACKGROUND OF THE INVENTION

The present invention relates generally to diagnostic imaging and, more particularly, to a system and method of preventing saturation of detectors during CT data acquisition, correcting over-ranging CT detectors, and verifying the precision of a CT view correction.

Typically, in radiographic systems, an x-ray source emits x-rays toward a subject or object, such as a patient or a piece of luggage. Hereinafter, the terms "subject" and "object" may be interchangeably used to describe anything capable of being imaged. The x-ray beam, after being attenuated by the subject, impinges upon an array of radiation detectors. The intensity of the radiation beam received at the detector array is typically dependent upon the attenuation of the x-rays through the scanned object. Each detector of the detector array produces a separate signal indicative of the attenuated beam received by each detector. The signals are transmitted to a data processing system for analysis and further processing which ultimately produces an image.

In a similar fashion, radiation detectors are employed in emission imaging systems such as used in nuclear medicine (NM) gamma cameras and Positron Emission Tomography (PET) systems. In these systems, the source of radiation is no longer an x-ray source, rather it is a radiopharmaceutical introduced into the body being examined. In these systems each detector of the array produces a signal in relation to the localized intensity of the radiopharmaceutical concentration in the object. Similar to conventional x-ray imaging, the strength of the emission signal is also attenuated by the inter-lying body parts. Each detector element of the detector array produces a separate signal indicative of the emitted beam received by each detector element. The signals are transmitted to a data processing system for analysis and further processing which ultimately produces an image.

In most computed tomography (CT) imaging systems, the x-ray source and the detector array are rotated about a gantry encompassing an imaging volume around the subject. X-ray sources typically include x-ray tubes, which emit the x-rays as a fan or cone beam from the anode focal point. X-ray detector assemblies typically include a collimator for reducing scattered x-ray photons from reaching the detector, a scintillator adjacent to the collimator for converting x-rays to light energy, and a photodiode adjacent to the scintillator for receiving the light energy and producing electrical signals therefrom. Typically, each scintillator of a scintillator array converts x-rays to light energy. Each photodiode detects the light energy and generates a corresponding electrical signal. The outputs of the photodiodes are then transmitted to the data acquisition system and then to the processing system for image reconstruction.

Conventional CT imaging systems utilize detectors that convert x-ray photon energy into current signals that are integrated over a time period, then measured and ultimately digitized. A drawback of such detectors is their inability to provide independent data or feedback as to the energy and incident flux rate of photons detected. That is, conventional CT detectors have a scintillator component and photodiode component wherein the scintillator component illuminates upon reception of x-ray photons and the photodiode detects illumination of the scintillator component and provides an integrated electrical current signal as a function of the intensity and energy of incident x-ray photons. While it is generally recognized that CT imaging would not be a viable diagnostic imaging tool without the advancements achieved with conventional CT detector design, a drawback of these integrating detectors is their inability to provide energy discriminatory data or otherwise count the number and/or measure the energy of photons actually received by a given detector element or pixel. Accordingly, recent detector developments have included the design of an energy discriminating detector that can provide photon counting and/or energy discriminating feedback. In this regard, the detector can be caused to operate in an x-ray counting mode, an energy measurement mode of each x-ray event, or both.

These energy discriminating detectors are capable of not only x-ray counting, but also providing a measurement of the energy level of each x-ray detected. While a number of materials may be used in the construction of an energy discriminating detector, including scintillators and photodiodes, direct conversion detectors having an x-ray photoconductor, such as amorphous selenium or cadmium zinc telluride, that directly convert x-ray photons into an electric charge have been shown to be among the preferred materials. A drawback of photon counting detectors is that these types of detectors have limited count rates and have difficulty covering the broad dynamic ranges encompassing very high x-ray photon flux rates typically encountered with conventional CT systems. Generally, a CT detector dynamic range of 1,000,000 to one is required to adequately handle the possible variations in photon flux rates encountered in CT imaging. In the fast scanners now available, it is not uncommon to encounter x-ray flux rates of over 108 photons/mm2/sec when no object is in the scan field, with the same detection system needing to count only tens of photons that manage to traverse the center of large objects.

The very high x-ray photon flux rates ultimately lead to detector saturation. That is, these detectors typically saturate at relatively low x-ray flux levels. This saturation can occur at detector locations wherein small subject thickness is interposed between the detector and the radiation source or x-ray tube. It has been shown that these saturated regions correspond to paths of low subject thickness near or outside the width of the subject projected onto the detector array. In many instances, the subject is more or less cylindrical in the effect on attenuation of the x-ray flux and subsequent incident intensity to the detector array. In this case, the saturated regions represent two disjointed regions at extremes of the detector array. In other less typical, but not rare instances, saturation occurs at other locations and in more than two disjointed regions of the detector. In the case of a cylindrical subject, the saturation at the edges of the array can be reduced by the imposition of a bowtie filter between the subject and the x-ray source. Typically, the filter is constructed to match the shape of the subject in such a way as to equalize total attenuation, filter and subject, across the detector array. The flux incident to the detector is then relatively uniform across the array and does not result in saturation. What can be problematic, however, is that the bowtie filter may not be optimum given that a subject population is significantly less than uniform and not exactly cylindrical in shape nor centrally located in the x-ray beam. In such cases, it is possible for one or more disjointed regions of saturation to occur or conversely to over-filter the x-ray flux and unnecessarily create regions of very low flux. Low x-ray flux in the projection results in a reduction in information content which will ultimately contribute to unwanted noise in the reconstructed image of the subject.

A number of techniques have been proposed to address saturation of any part of the detector. These techniques include maintenance of low x-ray flux across the width of a detector array, for example, by modulating tube current or x-ray voltage during scanning. However, this solution leads to increased scanned time. That is, there is a penalty in that the acquisition time for the image is increased in proportion to the nominal flux needed to acquire a certain number of x-rays that meet image quality requirements.

It would therefore be desirable to design a method and system to control x-ray flux on a CT detector assembly to reduce the likelihood of detector element saturation or over-ranging and, for those detector elements that do over-range, it would also be desirable to have a data correction technique for effectively and efficiently correcting saturated CT views.

BRIEF DESCRIPTION OF THE INVENTION

The present invention is a directed method and apparatus for reducing the occurrence of detector element saturation during CT data acquisition as well as effectively correcting the data associated with an over-ranging detector element that overcomes the aforementioned drawbacks.

An adaptive CT data acquisition technique is presented whereby radiation emitted for CT data acquisition is dynamically controlled to limit exposure to those detectors of a CT detector assembly that may be particularly susceptible to saturation during a given data acquisition. The data acquisition technique recognizes that for a given subject size and position that pre-subject filtering and collimating of a radiation beam may be insufficient to completely prevent detector element saturation. As such, the present invention also includes implementation of a number of CT data correction techniques for correcting otherwise unusable data of a saturated CT detector. These data correction techniques include a nearest neighbor correction, off-centered phantom correction, off-centered synthetic data correction, scout data correction, planar radiogram correction, and a number of others. The invention is particularly applicable with energy discriminating CT systems but is equivalently applicable with conventional CT systems as well as other multi-energy CT systems, such as dual kVp-based systems.

Therefore, in accordance with one aspect of the present invention, a method of CT data correction includes acquiring CT data from an object and comparing a profile of the CT data to an off-centered phantom profile. The method further includes correcting saturated portions of the CT data from the off-centered phantom profile. Moreover, off-centered phantom profiles used for correction may alternatively be generated using analytic means based on object geometry and predicted material/x-ray interactions to generate synthetic profile data of the required size, geometry and material.

According to another aspect, the present invention includes a CT imaging system and a computer program installed thereon and representing a set of instructions that when executed by a computer causes the computer to correct saturated portions of the CT data from the off-centered phantom profile. Moreover, off-centered phantom profiles used for correction may alternatively be generated using analytic means based on object geometry and predicted material/x-ray interactions to generate synthetic profile data of the required size, geometry and material.

In accordance with another aspect, the present invention includes a computer readable storage medium having a computer program stored thereon and representing a set of instructions that when executed by a computer causes the computer to normalize signal values for each detector element of a CT detector. The computer program further compares a signal value for a detector element to a pair of thresholds, characterizes a CT view corresponding to the signal value of a given detector as one of a normal view, a noisy view, and a saturated view from the comparison, and applies a filter kernel to the CT view if the CT view is characterized as a noisy view. The computer program applies a saturated view correction to the CT view if the CT view is characterized as a saturated view.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
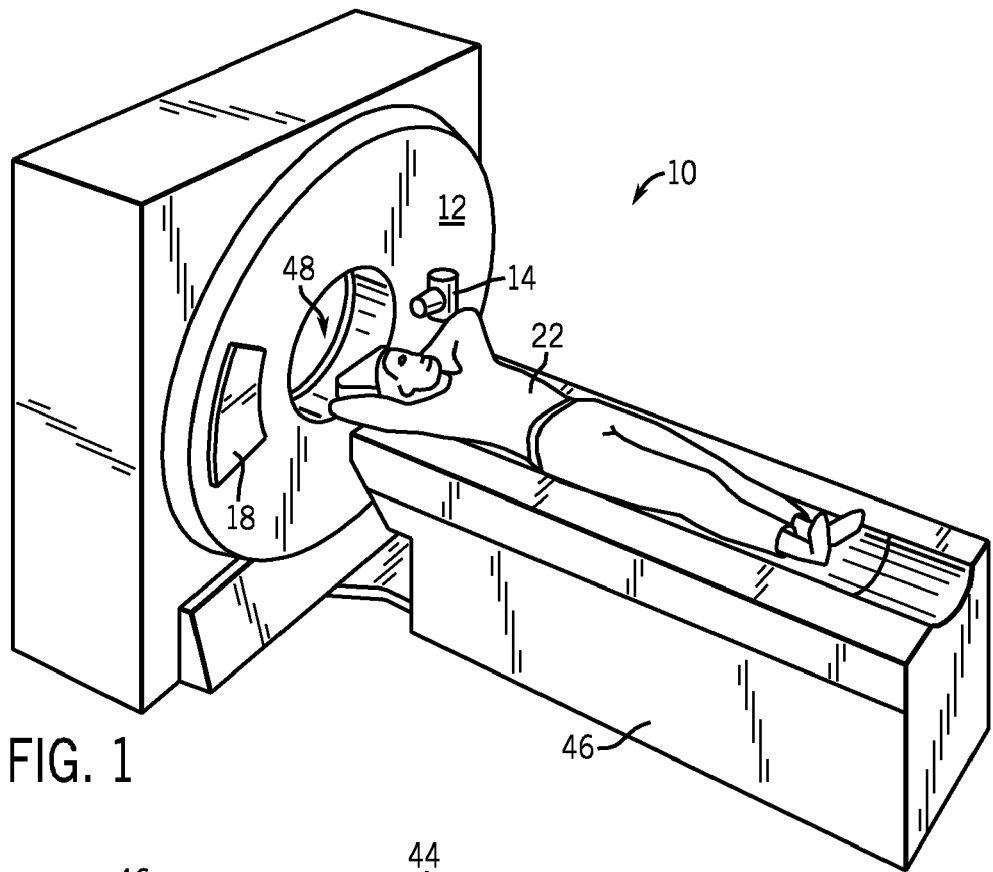
FIG. 1 is a pictorial view of a CT imaging system.
Figure 2:
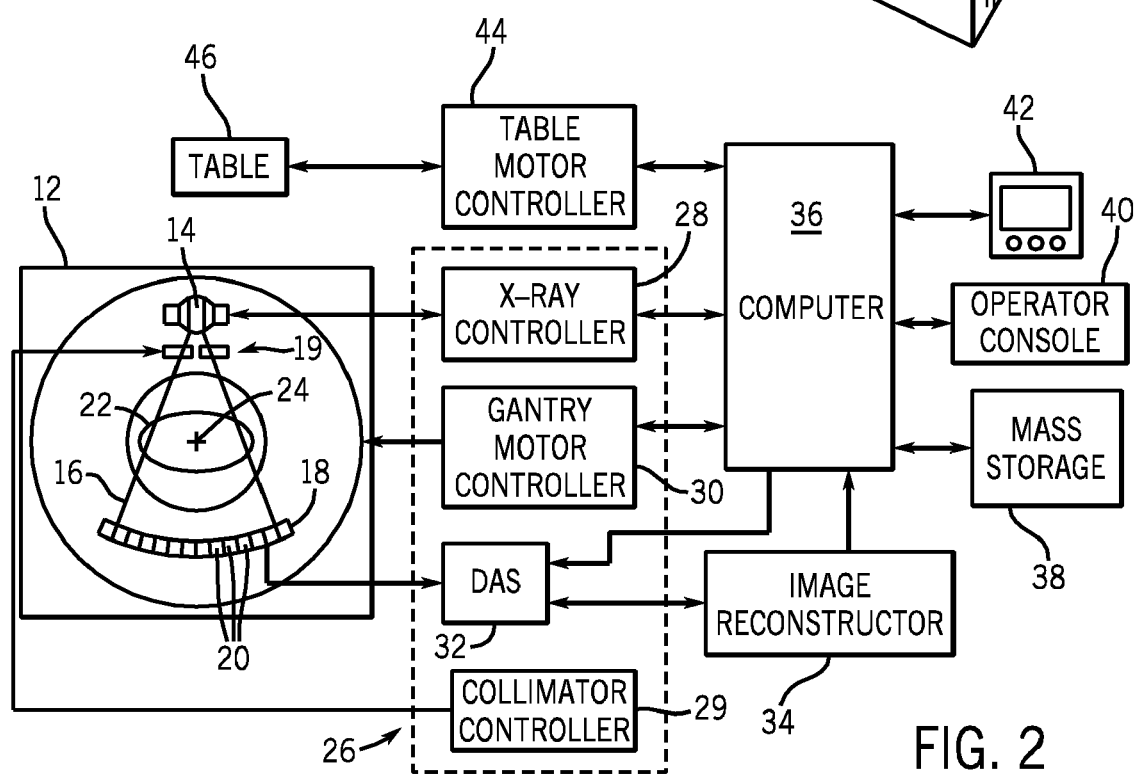
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 on the opposite side of the gantry 12. The beam of x-rays is collimated by a collimator 19. Detector assembly 18 is formed by a plurality of detectors 20 which together sense the projected x-rays that pass through a medical patient 22. Each detector 20 produces an electrical signal that represents the intensity of an impinging x-ray beam and may also be capable of providing photon or x-ray count data and energy level, and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14, a gantry motor controller 30 that controls the rotational speed and position of gantry 12, and a collimator controller 29 that controls collimator 19 to collimate the x-ray beam in the x (as shown in FIG. 2). A data acquisition system (DAS) 32 in control mechanism 26 reviews data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated display screen 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

The present invention includes an x-ray flux management control designed to prevent saturation of detector elements characterized by low dynamic range such as in photon counting/energy discriminating x-ray detection systems. Dynamic range of a detector channel defines the range of x-ray flux levels that the detector channel can handle to provide meaningful data at the low-flux end and not experience over-ranging or saturating at the high flux end. Notwithstanding the need to prevent over-ranging, to provide diagnostically valuable data, the handling of low-flux conditions, which commonly occur during imaging through thicker cross-sections and other areas of limited x-ray transmission, is also critical in detector design. As such, the x-ray flux management control described herein is designed to satisfy both high flux and low flux conditions.

Figure 3:
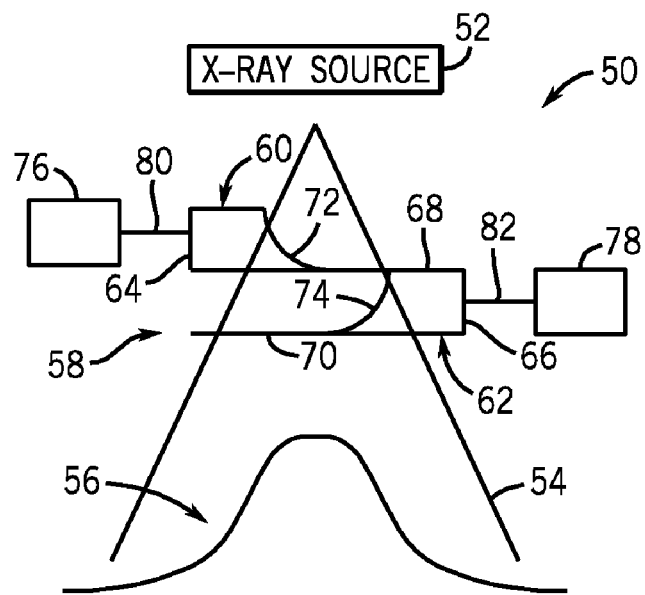
FIG. 3 is a schematic view of one embodiment of a pre-subject, beam shaping filter assembly applicable with the CT imaging systems illustrated in FIGS. 2-3.

Referring now to FIG. 3, an x-ray generation and filtering assembly applicable with the CT system described above is schematically shown. Assembly 50 includes an x-ray source 52 that projects a beam of x-rays 54, or other high frequency electromagnetic energy beam toward a subject (not shown). As will be described, beam 54 has a profile 56 that is tailored to at least approximate physical characteristics, e.g. shape, of the subject. Attenuating the x-ray beam 54 prior to attenuation by the subject to define profile 56 is a pre-subject, beam-shaping filter assembly 58.

Filter assembly 58 includes a pair of filters or filter components 60 and 62 that generally mirror each other in shape and orientation. In this regard, each filter 60, 62 constitutes roughly one-half of the filter assembly. Each filter is defined by a base 64, 66, a tail 68, 70, and a curved or arcuate portion 72, 74. In this regard, attenuation of x-rays by each filter is non-uniform across the filter body. That is, since the base of each filter is thicker than the tail of each filter, the bases of each filter attenuate more x-rays than the tails of each filter. In one embodiment, the base of each filter has a thickness of 30 mm and each tail has a thickness of 0.25 mm. The degree of attenuation is function of the attenuation material used to fabricate the filter and the relative thickness of each filter portion.

Each filter 60, 62 is operationally connected to a motor assembly 76, 78, respectively. Each motor assembly receives control signals from a controller and/or computer of the imaging system, that when received, causes each motor assembly to position a respective filter in the x-ray beam or path 54. In one embodiment, each motor assembly includes a stepper motor, but it is contemplated that other types of motors may be used to position the filters. The motor assemblies 76, 78 are also designed to re-position the filters independently throughout data acquisition. In this regard, each filter may be separately and dynamically controlled or positioned to achieve a particular attenuation profile 56 throughout data acquisition. Moreover, it is preferred that both filters are connected and controlled by a respective motor assembly. Additionally, one filter could be fixed and remain stationary to the other filter. It is further contemplated that more than two filters may be used.

In an exemplary embodiment, the distal end (relative to the x-ray source) of filter 60 is 117 mm from the x-ray source 52. The distal end of filter 62 is set at 148 mm from the x-ray source in this exemplary embodiment. Additionally, in this exemplary embodiment, the base of filter 60 has a length along the x-axis of 45 mm, the tail has a length of 135 mm, and the connecting curved portion has a length of 24.9 mm. In contrast, the base of filter 62 has a length in the x-direction of 53 mm, the tail has a length of 168 mm, and the connected curved portion has a length of 34.2 mm. The dimensions of each curved portion are set forth in the table below. One skilled in the art will readily appreciate that the above dimensions are illustrative of only one of a number of possible embodiments.

Curvature X, Y Coordinate Dimensions

| Filter 96 X | Filter 96 Y | Filter 98 X | Filter 98 Y |
| --- | --- | --- | --- |
| 0.00000 | 0.140964 | 0.00000 | 0.140964 |
| 1.52658 | 0.277455 | 1.92109 | 0.277455 |
| 3.02431 | 0.736801 | 3.81409 | 0.736801 |
| 4.48315 | 1.49686 | 5.66911 | 1.49686 |
| 5.89467 | 2.53118 | 7.47786 | 2.53118 |
| 7.25198 | 3.81159 | 9.23358 | 3.81159 |
| 8.54973 | 5.30908 | 10.9311 | 5.30908 |
| 9.78406 | 6.99454 | 12.5666 | 6.99454 |
| 10.9524 | 8.83954 | 14.1378 | 8.83954 |
| 12.0536 | 10.8169 | 15.6436 | 10.8169 |
| 13.0874 | 12.9009 | 17.0839 | 12.9009 |
| 14.0545 | 15.0681 | 18.4596 | 15.0681 |
| 14.9562 | 17.2971 | 19.7722 | 17.2971 |
| 15.7946 | 19.5688 | 21.0238 | 19.5688 |
| 16.5720 | 21.8668 | 22.2169 | 21.8668 |

-continued

| Filter 96 X | Filter 96 Y | Filter 98 X | Filter 98 Y |
|---|---|---|---|
| 17.2910 | 24.1766 | 23.3544 | 24.1766 |
| 17.9543 | 26.4862 | 24.4391 | 26.4862 |
| 18.8075 | 27.9529 | 25.7168 | 27.9529 |
| 19.8335 | 28.7495 | 27.1705 | 28.7495 |
| 20.9281 | 29.2923 | 28.6963 | 29.2923 |
| 22.0739 | 29.6668 | 30.2769 | 29.6668 |
| 23.2688 | 29.9013 | 31.9104 | 29.9013 |
| 24.5186 | 29.9983 | 33.6029 | 29.9983 |

Motor assemblies 76, 78 axially and independently position filters 60, 62, respectively, so that the collective attenuation of the filters defines a target attenuation profile. In one embodiment, each motor positions a respective filter by extending and retracting respective piston assemblies 80 and 82. One skilled in the art will appreciate that other assemblies may be used to extend and retract the filters into and from the x-ray path. Based on the positioning of the filters, the attenuation caused by filter 60 is added to the attenuation caused by filter 62. Since each filter has a contour that defines a multiple thickness, the combined contours collectively define a multitude of possible beam profiles. A particular beam profile may therefore be selected from the multitude of possible beam profiles so that that the resulting beam profile is tailored to the particular patient or subject. That is, filters 60, 62 may be positioned relative to one another by their respective motor assemblies 76, 78 to define a beam profile that substantially matches an approximate shape of the patient, and, as a result, maintains a relatively uniform x-ray flux across the detector assembly. Also, filters 60, 62 are shown as at least partially overlapping one another. It is contemplated, however, that the filters be positioned such that no overlapping occurs.

While it is contemplated that a variable bowtie filter that can be matched to a subject size and position can be used to achieve relatively uniform x-ray flux across a CT detector assembly, it is recognized that fixed bowtie filters may also be used. In this regard, the CT system may be equipped with multiple bowtie filters and based on a scout scan or other form of measurement, the subject size and position can be ascertained and the appropriate bowtie filter from the library of filters can be selected. In one preferred embodiment, the bowtie filter is selected based on information acquired during a scout scan, such as a lateral or AP scout. Notwithstanding the robustness provided by a variable bowtie filter or maintenance of a library of fixed bowtie filters, it remains possible for acquired CT views to be corrupted or saturated.

For instance, given a bowtie filter constructed to provide uniform x-ray flux across a detector assembly during imaging of a circular object having a radius, R. The thickness of the bowtie filter along its length, x, may be characterized by the expression: $2R[1-\sqrt{1-x^2/R^2}]$. The family of available bowtie filters available may range from a radius of 5 cm to 45 cm. Generally, the filter radius is matched to the median width through a subject to be imaged. (Scout data may be used to determine the median width.) If a small R bowtie filter relative to the subject median width is selected, few saturated views would be expected; however, noise may increase as a result of the aggressive filtering of the radiation. That is, some CT views may experience such low photon statistics that the relevant information lost. These views are considered corrupted. On the other hand, if a large R bowtie filter is selected, detector saturation may occur for a number of detector elements notwithstanding that good photon statistics are available for non-saturated detector elements. Both of which are possible despite selection of a bowtie filter selected to maintain a relatively uniform x-ray flux across the CT detector assembly. That is, through either application of a fixed bowtie filter or the imprecision of a variable bowtie filter, some CT views may be corrupted or saturated. These CT views introduce noise, streaks, and artifacts (such as beam hardening artifacts) into the reconstructed image.

Figure 4:
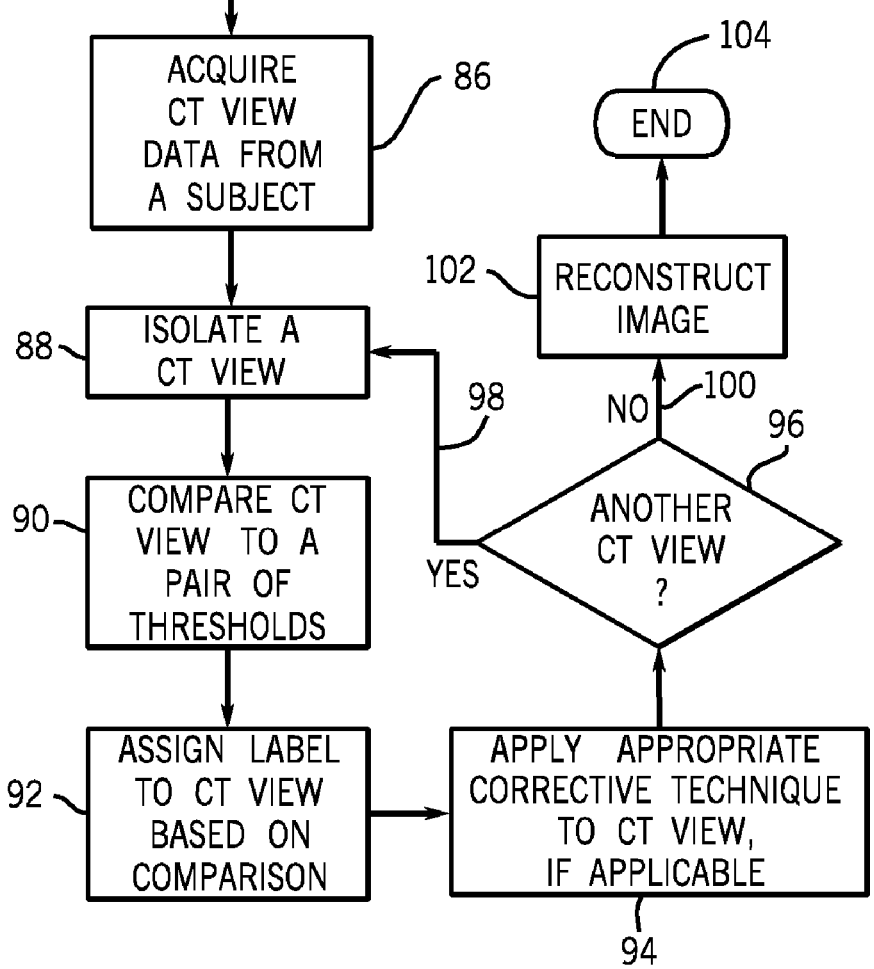
FIG. 4 is a flow chart setting forth the steps of a CT view characterization technique in accordance with one aspect of the present invention.

Accordingly, the present invention also includes implementation of post-acquisition processes to accommodate noisy and corrupted or saturated views. In this regard, the present invention also includes an iterative process for classifying a CT view as noisy, corrupted, or neither. The steps of this iterative process are illustrated in FIG. 4.

The process begins at 84 with the acquisition of CT data from an object or subject at 86. The CT data or CT views are acquired in a conventional manner and may be acquired with a conventional CT system or a multi-energy CT system. While energy discriminating CT detectors are more prone to saturation, the process may be implemented with conventional CT detector-based systems as the detectors of these systems may also saturate, albeit at higher flux rates than energy discriminating detectors. Once the CT views have been acquired 86, a CT view is isolated and selected for correction 88. The data contained in the selected CT view is then compared to a pair of thresholds at 90. More particularly, each CT view has a value, such as a photon count or signal strength, that can be compared to thresholds for view classification purposes. The CT view value may be a raw value or normalized with respect to all other CT views or a base measure. The pair of thresholds are used to define a given CT view (or the detector element associated with the given CT view) as noisy, saturated, or neither. Generally, the smaller the CT view value, the noisier the view, i.e. fewer photons detected. In this regard, if the CT view value is less than a first threshold the CT view is characterized as a noisy view. On the other hand, if the CT view value is greater than both thresholds, the CT view is characterized as a corrupted or saturated view. If the CT view value exceeds the first threshold and is less than the second threshold the CT view is characterized as a normal view not in need of filtering or correction. Accordingly, the CT view selected at 88 is assigned a label at 92 based on the characterization afforded the selected view. If the CT view is labeled as normal, i.e. not needing correction or filtering, corrective measures are not carried out on the CT view. If the CT view is labeled as a noisy CT view, then an appropriate filtering process is applied at 94.

More specifically, an adaptive filter kernel is applied to the CT view labeled noisy to reduce noise in the CT view at the expense of spatial resolution. In this regard, the CT view is filtered to remove noise therein, but a byproduct of the noise-removal process is a loss of spatial resolution. It is contemplated that the type, strength, and scope of the kernel applied can be tied to the CT view value. That is, the CT view is smartly filtered based on the level to achieve an acceptable intersection between noise reduction and spatial resolution. It is contemplated, however, that a fixed kernel could also be applied for each noisy CT view regardless of the degree of noise in the CT view.

It is also contemplated that a nearest neighbor correction may also be applied to correct a noisy CT view. In this regard, the photon count of the noisy CT view can be determined directly from photon count data output by a photon counting CT detector element or empirically estimated from knowledge of detector element construction and the CT view value, i.e. signal strength. That is, the number of photons, N, can be ascertained from the detected signal, S, for the CT view. The signal value, S, may then be replaced with a signal value, S', obtained from the mean of n nearest neighboring detector elements, as set forth in the following expression: S'=sum(Si)/n. This averaging of the n nearest neighbors spatially filters the noisy CT view to decrease noise in the CT view.

If the selected CT view is labeled as corrupted or saturated, an appropriate corrective process is carried out on the CT view at 94 as well. While a number of saturation correction techniques are contemplated, a number of exemplary techniques will be described in greater detail below.

Once the noisy or corrupted CT view has been appropriately filtered or corrected, a determination is made at 96 as to whether another CT view is to be analyzed. If so 96, 98, the process returns to step 88 with selection of a CT view for inspection. If not 96, 100, an image is reconstructed in a conventional manner 102 and the process ends at 104. It is recognized that all CT views may be processed to associate a given label with each CT view. It also contemplated that only those CT views associated with detector elements having a propensity to output noisy or saturated data are evaluated so as to expedite the reconstruction process.

Hereinafter, a number of CT view correction techniques will be described. These techniques are implement-able with conventional CT systems as well as multi-energy CT systems, such as dual energy kvp, energy discriminating, and photon counting systems. Generally speaking, each of the techniques is directed to the correction of a corrupted or saturated CT view with data of a non-corrupted or non-saturated CT view. The non-corrupted or non-saturated CT data used for corrective purposes may be acquired in a scout scan, imaging scan, or ascertained from a phantom profile and, in particular, an off-centered water profile. Alternatively, the phantom profile may be replaced by analytically determined synthetic profiles based on object geometry and material.

One corrective technique utilizes one or more planar scout scans (radiograms) to provide an indication of x-ray absorption at the edges of a subject to be imaged. A scout scan or planar radiogram is routinely utilized as a predictive tool for CT procedures. The scout scan is regularly carried out with a radiation dose much lower than axial or helical imaging scans. Generally, the radiation dose for a scout scan is one-tenth of the dose used for a normal axial or helical imaging scan. At this low x-ray flux level, CT detectors do not typically saturate or overrange during the acquisition of scout data. Additionally, the scout scan data is linked to precisely match the views of imaging data acquired during an axial or helical scan. The prerequisite for matching the views between the several scans is table position and view angle. In this fashion, an individual fan view in an axial or helical scan may be precisely matched to an unsaturated scout view. As a result, the axial or helical view can be corrected for data corruption or data saturation with a corresponding scout view. Additionally, the scout view data may be used to correct neighboring saturated or corrupted views.

Figure 5:
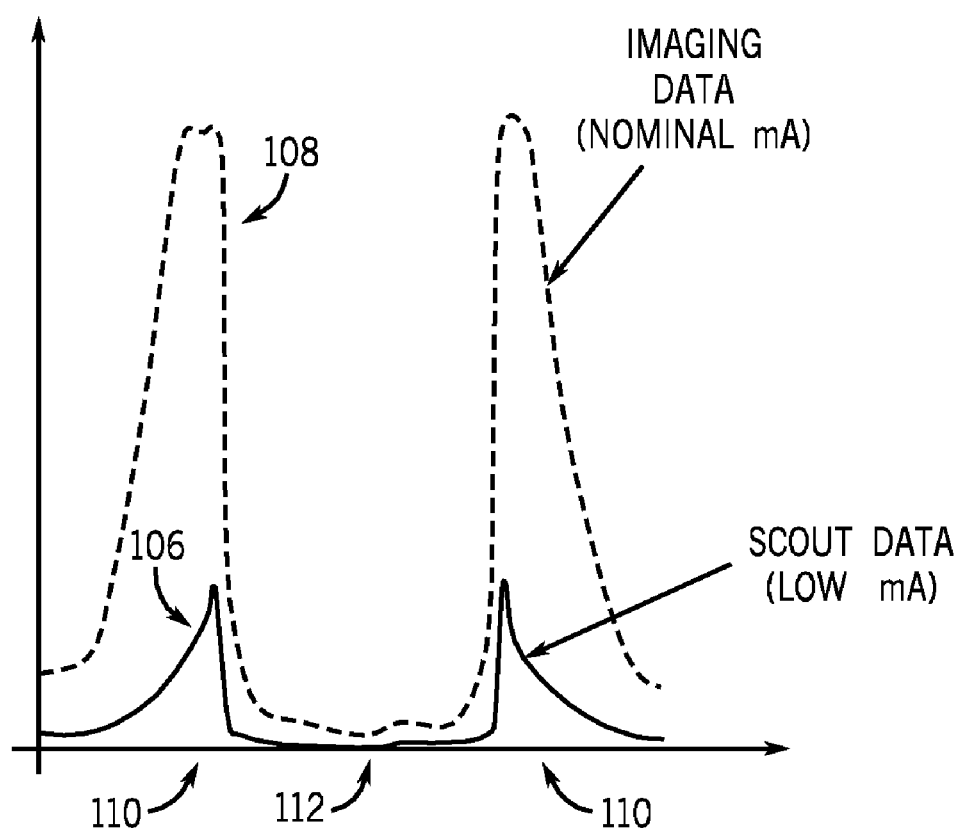
FIG. 5 is a graph illustrating a scout dose profile relative to an imaging dose profile.

This technique is schematically illustrated in FIG. 5. FIG. 5 illustrates a scout dose profile 106 (low mA) relative to an imaging dose profile 108 (nominal or imaging mA). As shown, the dose profiles may be relative symmetrical, but the imaging dose profile 108 has greater amplitude than scout dose profile 106. As a result, at the edges of the subject, generally referenced 110, radiation dose or flux greatly exceeds the dose or flux corresponding to the central region of the subject, generally referenced 112. This disparity in the x-ray flux at the edges relative to the central regions may cause corruption or saturation of detector elements positioned at the edges of the subject during an imaging scan. Saturation is prevented during the acquisition of scout data by using a tube current sufficiently low so as not to cause detector saturation. That is, the peaks of the scout dose profile 106 are insufficient to cause detector over-ranging.

Figure 6:
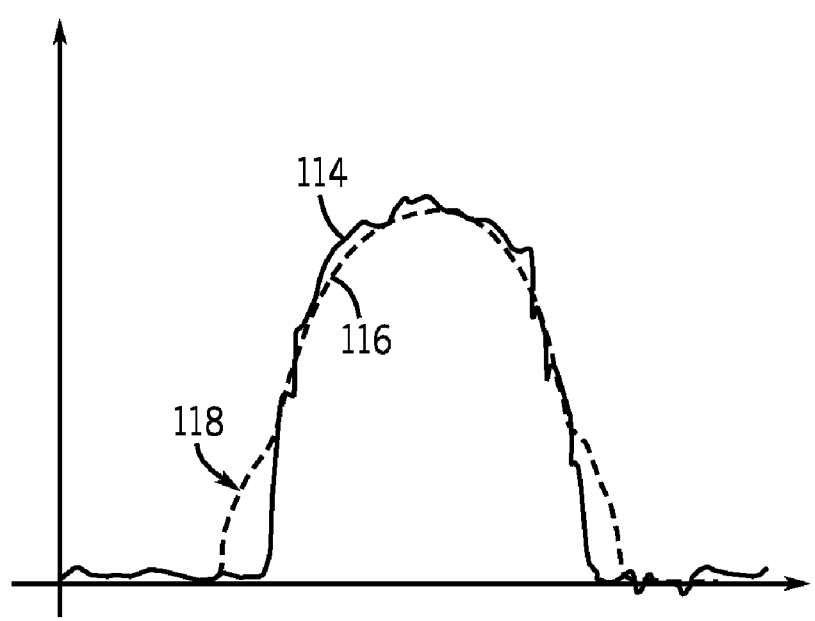
FIG. 6 is graph illustrating a scout fan matched to an imaging fan.

When an axial or helical scan is executed, the scout fans and the axial/helical fans (having the same angle and position) are matched to one another. This is illustrated in FIG. 6. As shown, the preprocessed view data, ln(Ibody/Iair) for a scout scan 114 is matched to axial and/or helical imaging data 116. Therefore, as described below, data from an unsaturated view can be used to correct a corrupted or saturated axial or helical view 118. Given that the integral sum (or total) of preprocessed projection rays for an object, $\Sigma=\ln(I_{body}/I_{air})$, for a given plane, is constant and independent of view angle, data for other fan angles not matching the available scout scan data can be approximated. Subsequently, a view with saturated readings may be approximated and corrected using scout scan readings. Furthermore, the scout data can be used to extract the subject or object dimensions (cross-sectional height and width) and position in the scan field-of-view (FOV). It is also contemplated that correction data can be determined from multiple scout scans, such as two orthogonal scout scans, i.e. an AP and a lateral scout.

Figure 7:
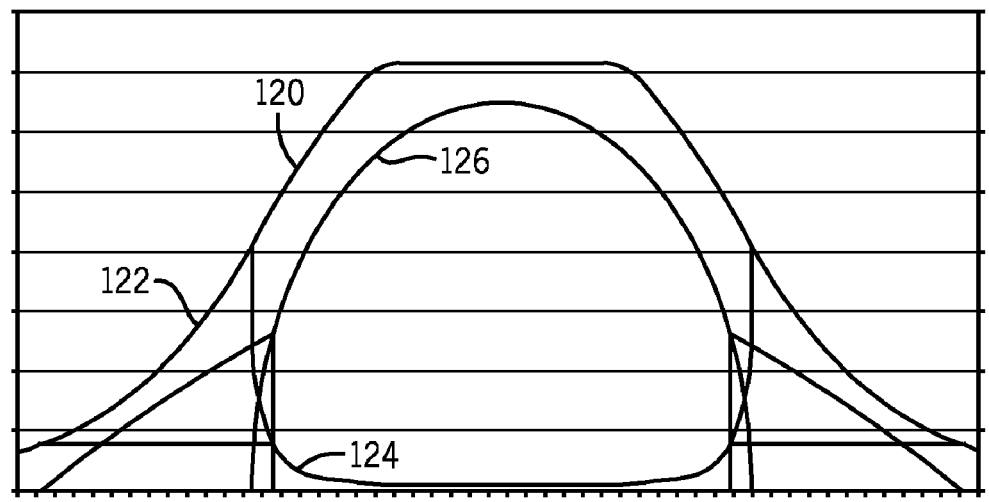
FIG. 7 illustrates a number of exemplary radiation profiles that may be encountered in a CT data acquisition.

As referenced above, detector element saturation often occurs near the edges of the object to be imaged. This is largely attributable to that most subjects that are imaged using CT technology are medical patients. Patients typically having an elliptical cross-section with their extremities being thinner than the other anatomical sections, e.g. torso. In this regard, CT data correction is primarily focused on restoring a relatively small number of detector elements as illustrated in FIG. 7. Plot 120 illustrates a free transmission profile as radiation passes through a bowtie filter. Plot 122 represents the synthetic raw profile of radiation through the bowtie filter and a cylindrically shaped object. Plot or curve 124 represents scan data profile where detector dynamic range is limited such that saturation occurs only at one-eighth of the free air signal. Therefore, the preprocessed data after air correction ln(Ibody/Iair), represented by plot 126, indicates that aside from detectors exposed to free air transmission, significant saturation occurs in only a small number of detectors. In this regard, saturated data readings typically occur in the presence of an overwhelmingly large number of unsaturated data readings. As will be described, this phenomenon will be exploited to correct saturated readings.

Figure 8:
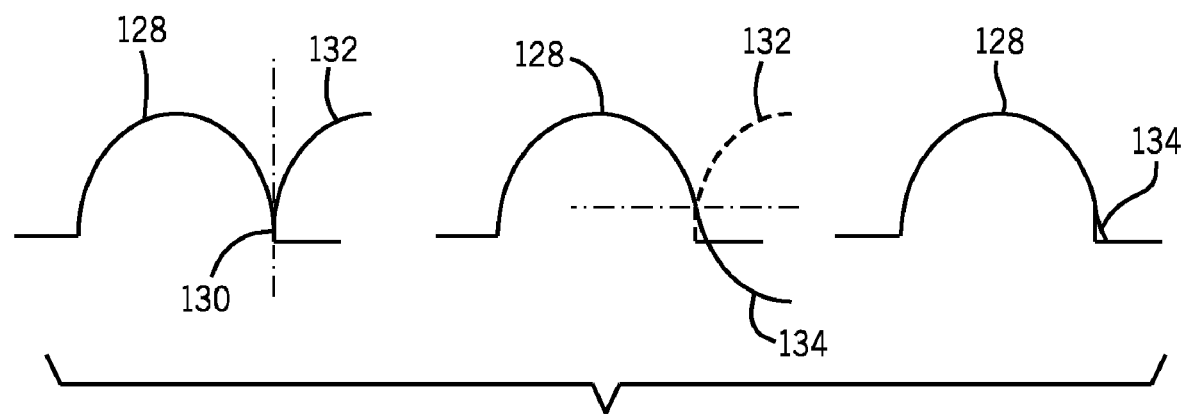
FIG. 8 is a schematic illustrating one exemplary saturation data correction technique in accordance with the present invention.

One such corrective technique is illustrated in FIG. 8. This corrective technique utilizes known unsaturated data to determine "unsaturated" readings for otherwise saturated detectors or detector elements. In this regard, unsaturated view data 128 adjacent to saturated view data region 130 is used to extrapolate values across the saturated data region. The unsaturated view data 128 is flipped about the saturated view data region 130 to yield a first mirror of view data 132. View data 132 is then mirrored again, but about itself to yield view data 134. View data 134 is then clipped at the zero value limit. As a result of this "double-flipping" and clipping, a smooth and continuous extension of the unsaturated view data 128 is provided for the saturated view data region. Accordingly, unsaturated readings are available for the saturated data region and may be used for image reconstruction.

To maintain image quality, an additional scaling or windowing of the newly estimated data may also be done in order to modify the manner in which the estimated data approaches the subject border or zero prep value. Various windowing methods may be employed including a window that drops off in a linear or squared fashion relative to the radial distance from the last known detector element value. A further enhancement would be to use scout data to determine the actual subject diameter, and use this information to constrain the scaling function to fulfill this requirement.

In known saturation correction paradigms, missing data is modeled by a centered cylindrical water object. Notwithstanding the robustness of these known paradigms, a cylindrical water object or phantom profile has been shown to assume a subject position and shape that is not optimal for a given subject and scan. Therefore, in accordance with another contemplated saturation correction technique, an off-centered water profile is used to provide a more accurate predictor of data acquisition from a given subject, and thus, a more accurate corrective measure. In addition to an off-centered cylindrical object profile, the present invention contemplates the use of off-centered elliptical object profiles to more accurately correct saturated data.

Figure 9:
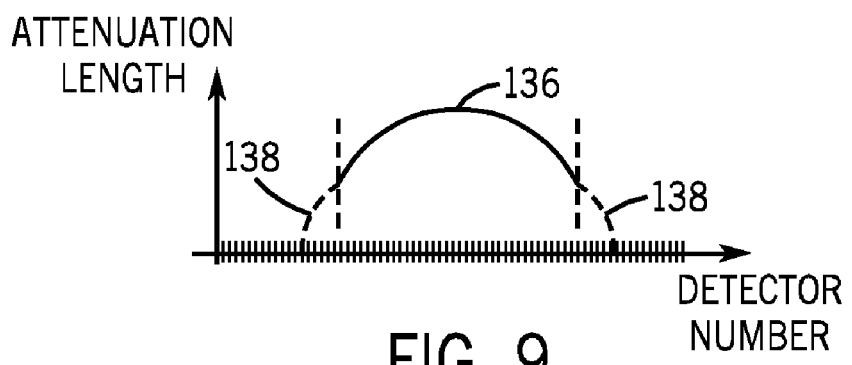
FIG. 9 is a graph illustrating an x-ray flux profile for a given subject to be imaged.
Figure 10:
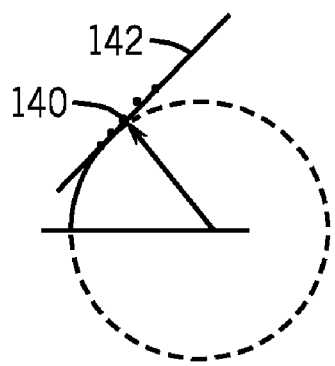
FIG. 10 is a schematic illustrating an exemplary technique of determining an off-centered profile to be used for saturated data correction.

As a precursor of selecting the appropriate the off-centered profile, subject shape and position must be derived. The present invention contemplates a number of techniques to derive this information. One such technique is illustrated in FIGS. 9 and 10. FIG. 9 illustrates an x-ray flux profile for a given subject. As illustrated, the non-saturated data corresponds to solid line 136 and the extrapolated data is represented by lines 138. The extrapolated data is unsaturated data that is used in the stead of saturated data. The extrapolated data is determined from an off-centered water profile that is selected based on subject shape and position.

Referring now to FIG. 10, the manner in which the appropriate off-centered profile is determined is schematically illustrated. Specifically, the radius to the last known (unsaturated) data 140 of the unsaturated data profile 136 (FIG. 9) is determined. More particularly, a line 142 is fit to a set of last known data points 140. The slope and the line-intercept of this line 142 are then used to determine the most appropriate non-centered cylindrical water or other phantom profile that should be used for data extrapolation. That is, either a library of non-centered profiles are kept in a database of the scanner and earmarked with a slope and intercept value, or pseudo profiles are computationally generated according to need. The slope and line-intercept values for the last known data values of the imaging data profile is used to select or generate mathematically the optimal corrective profile. Once obtained, missing data extrapolation is carried out using the profile in a conventional manner.

Figure 11:
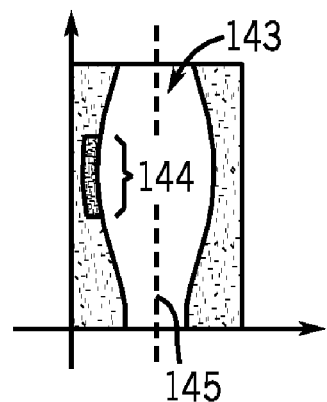
FIG. 11 is a schematic illustrating yet another technique of determining an off-centered profile for saturated data correction.

An enhancement to the above "line-fix" technique incorporates the shape of the sinogram edge to better determine which off-centered profile to use for missing data correction as illustrated in FIG. 11. A CT sinogram is a display of a slice of CT data before reconstruction. While not generally useful in clinical evaluations, a sinogram can be used to identify a corrupted or saturated region. The horizontal axis of a sinogram corresponds to the different x-rays in each projection. The vertical axis represents each projection angle. A horizontal line of the sinogram subsequently represents a view of x-ray data such as that shown in FIG. 9.

The first estimate of radius and offset is determined for each view according to last known unsaturated data as outlined above and added to the sinogram as that illustrated in FIG. 11. This radius determination is repeated for each saturated view of the sinogram 143. That is, in the illustrated sinogram, there exists a region of estimated unsaturated data 144. Accordingly, for each view in this region of estimated unsaturated data 144, a view radius is determined. The various radii are used to approximate edges, E, of the sinogram 143, i.e. distance from edge of sinogram to center detector, schematically shown as dashed line 145. A second order least squares fit is then made to the object edge. A second derivative, E", is then determined from the second order least squares fit. This second derivative value along with the distance of the phantom edge, E, to the center detector, is used to determine a radius of curvature R, defined by R=E+E". This radius of curvature may then be used to select or generate the appropriate off-centered profile for missing data correction.

The present invention also contemplates a hybrid of the subject shape and position techniques described with respect to FIGS. 9-11. In this hybrid technique, the "line-fix" technique described with respect to FIGS. 9 and 10 is used to determine a starting curvature at the onset of saturated data and the "curve-fix" technique described with respect to FIG. 11 is used to determine an ending curvature of the saturated data region. An average of the two curvatures is then used to determine an extrapolation radius. This extrapolation radius is then used to determine which off-centered profile to use for data correction.

Figure 12:
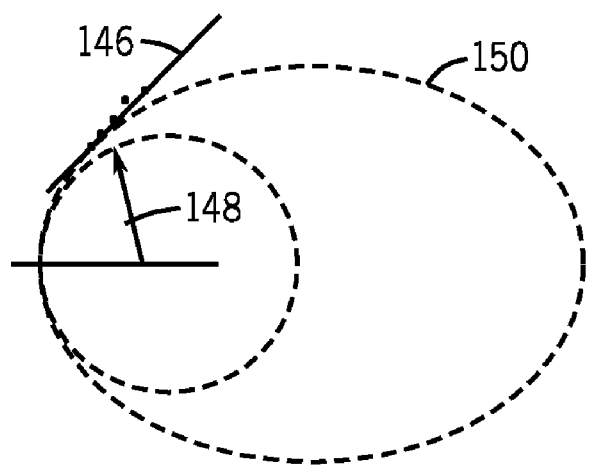
FIG. 12 is a schematic illustrating yet a further technique of determining an off-centered profile to be used for data correction.

As described above, known saturation data correction techniques have been predicated upon a cylindrical object profile. However, most subjects do not match a cylindrical profile. In this regard, the present invention also contemplates the implementation of elliptical object profiles for missing data correction. In FIG. 12, an "elliptical-fix" method is schematically shown for determining which elliptical object profile to use for data correction.

This "elliptical-fix" technique determines an extrapolation expression using a geometric combination of the "line-fix" and the "curve-fix" techniques described above. Specifically, the "line-fix" technique is used to determine a line 146 tangential to the last known data point of the unsaturated data region. The "curve-fix" technique is then used to determine a radius of curvature 148 of a cylindrical object. Therefrom, an elliptical shape 150 tangential to line 146 with the radius of curvature 148 is determined. As stated above, this elliptical shape is determined from a geometric combination of the tangential line 146 and the radius of curvature 148. Given the tangential line 146 having slope $\alpha$ and intercepting the ellipse at height h, and the required radius of curvature 148 being R, the required elliptical shape $$\frac{(x-s)^2}{a^2} + \frac{y^2}{b^2} = 1$$

is obtained where $$k = \tan(\alpha)$$

$$s = \frac{h^3 k}{R^2 - h^2 k^2}$$

$$a = \frac{h^2 R}{R^2 - h^2 k^2}$$

$$b = \frac{hR}{\sqrt{R^2 - h^2 k^2}}$$

Figure 13:
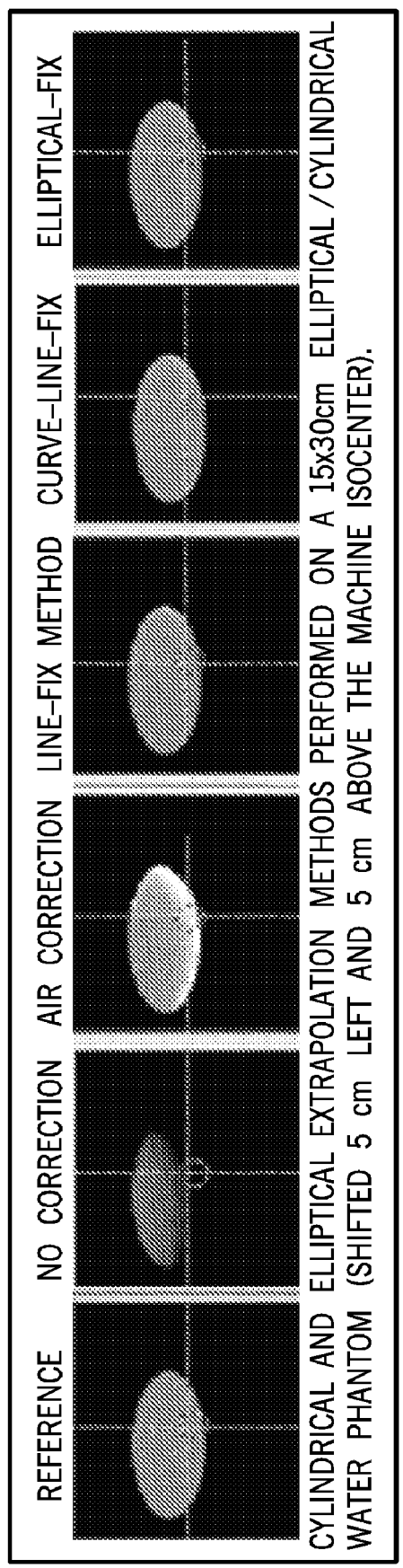
FIG. 13 illustrates a series of images that have been corrected in accordance with saturation correction techniques of the present invention shown relative to known correction techniques.

The results of the "line-fix", "curve-fix", and "elliptical-fix" techniques are illustrated in FIG. 13 for a 15×30 cm water phantom shifted 5 cm left and 5 cm above system iso-center. The "-fix" results are shown relative to a reference image, a "no correction" image, and an "air-correction" image. As shown, each of the "-fix" images provide a correction of otherwise saturated data that is not provided in the air corrected image. Moreover, the corrected images substantially match the reference image that was acquired at lower dose levels to avoid detector saturation.

In addition to using low-flux scout data for correction directly as described with respect to FIGS. 5 and 6, scout data may also be used to determine a "center of mass" of the subject to be imaged. For instance, a lateral scout scan may be used to acquire data to determine the y-position of the subject and an AP scout scan may be used to acquire data to determine the x-position of the subject. From this x and y positional information, the center of mass of the subject can be derived and used to select an appropriate off-centered profile for missing data correction.

In an approach similar to using the center of mass of a subject relative to a reference position in the CT scanner bore to determine subject position, the present invention also contemplates a center of mass calculus that is based exclusively on axial or helical scan data whereby subject center of mass is determined from 180 degree or 360 degree view data. This technique includes the determination of a "center of gravity", as defined by the expression [Σ(P·n)/Σn], for each preprocessed attenuation values $P=\ln(I_{body}/I_{air})$ in each view (n) and fitting the view-by-view results to a sine wave with the appropriate phase and amplitude. The phase and amplitude values determine the center of mass of the object in the scan FOV. The center of mass is then used to select the appropriate correction profile. Since saturated points are a small part of the views and the center of mass is determined by all the data points, replacing the saturated data with air-corrected values (where P=0) has been shown to have a negligible effect on center-of-mass estimations.

Figure 14:
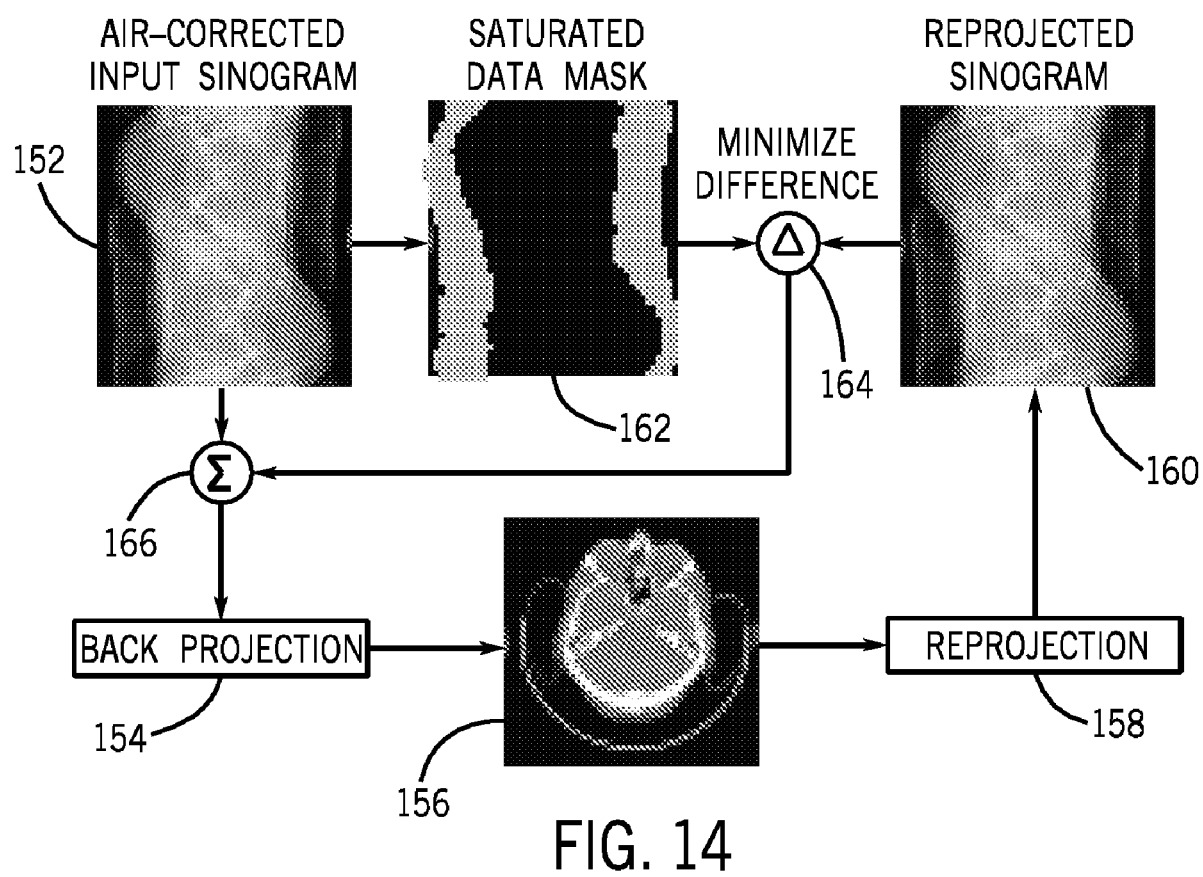
FIG. 14 is a schematic illustrating a technique for correcting saturated data in accordance with another aspect of the present invention.

Referring now to FIG. 14, an exemplary saturated data correction technique is illustrated. With this technique, saturated views are air corrected. That is, when detector element readings are saturated, the detector element data is set to air transmission values regardless of whether anatomical features were imaged by the detector element. This initial air correction of the saturated data yields an air-corrected input sinogram 152. The air-corrected sinogram is then backprojected 154 in the usual manner to reconstruct an image 156. Once the air-corrected image is generated, the image is reprojected 158 to obtain a second set of view data that is used to generate a reprojected sinogram 160. This reprojected sinogram 160 is then compared or masked with a saturated data mask 162 that is determined from the air-corrected sinogram 152. In one embodiment, the saturated data mask sinogram 162 includes only saturated data. In another embodiment, the mask sinogram 162 excludes all saturated data. In either case, the reprojected sinogram 160 and mask sinogram 162 are compared 164 to one another to determine a standard deviation between the air-corrected sinogram 152 and the reprojected sinogram 160. In short, the comparison 164 provides an improved estimate of the saturated data readings. The updated saturated data readings are then updated 166 onto the air-corrected sinogram whereupon the updated air-corrected sinogram is backprojected and an image reconstructed. The reprojection, comparison, and updating steps described above will be repeatedly carried out until the standard deviation between the reprojected sinogram and the air-corrected sinogram has converged to within a minimum standard deviation. Once this convergence occurs, the last-updated input sinogram is backprojected and an image for clinical analysis is reconstructed.

Heretofore, a number of corrective techniques have been described. The present invention also includes a number of techniques to verify the precision of a corrected view. In a saturation correction verification technique according to the present invention, an integral-view-summation view extension is used. This approach takes advantage of a property of equal spaced parallel view sinogram data. Specifically, the integral of the data of each view remains constant independent of view angle. As such, if there is a single unsaturated view, the integral of this view may be determined and used as a constant to which all other integrated view data is matched. That is, if an approximation is used to determine missing data for a saturated view, then this constant provides an additional test to verify the precision of the approximation. In this regard, the integral for an approximation can be compared to the integral constant to determine whether the approximation is a good approximation of the otherwise saturated data. If not, a new or different corrective calculus can be applied rather than reconstructing an image with poorly approximated corrected data. Additionally, the view-integral constant can be determined from imaging data or from scout data corresponding to the appropriate table position. Furthermore, the verification technique can be implemented with parallel-view sinograms as well as fan-beam sinograms.

Figure 15:
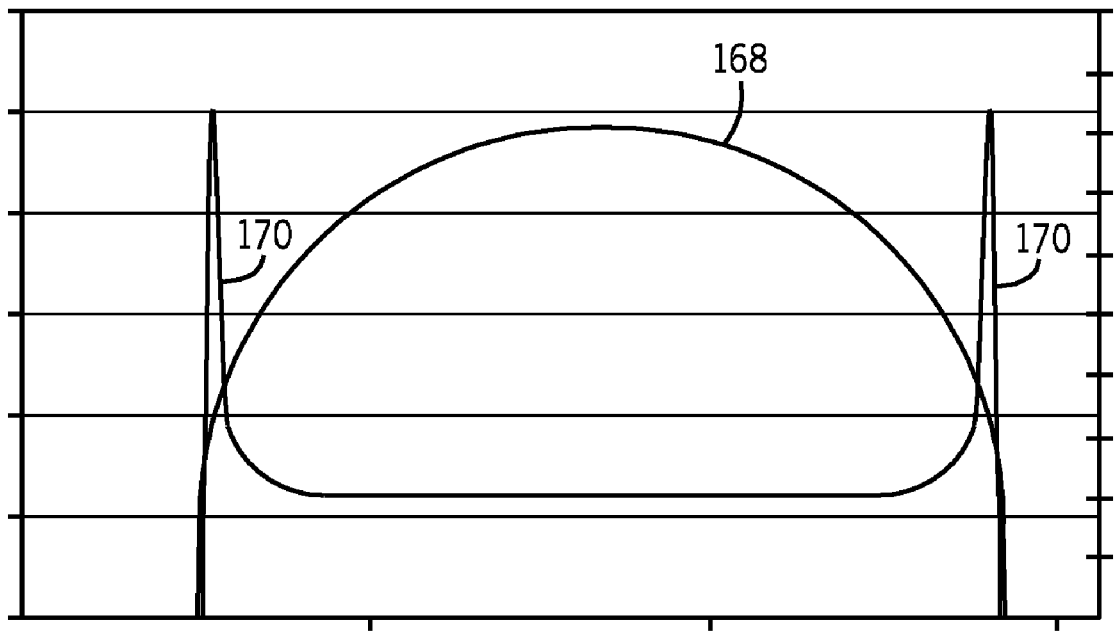
FIG. 15 is a graph illustrating a saturated data profile relative to an unsaturated data profile.
Figure 16:
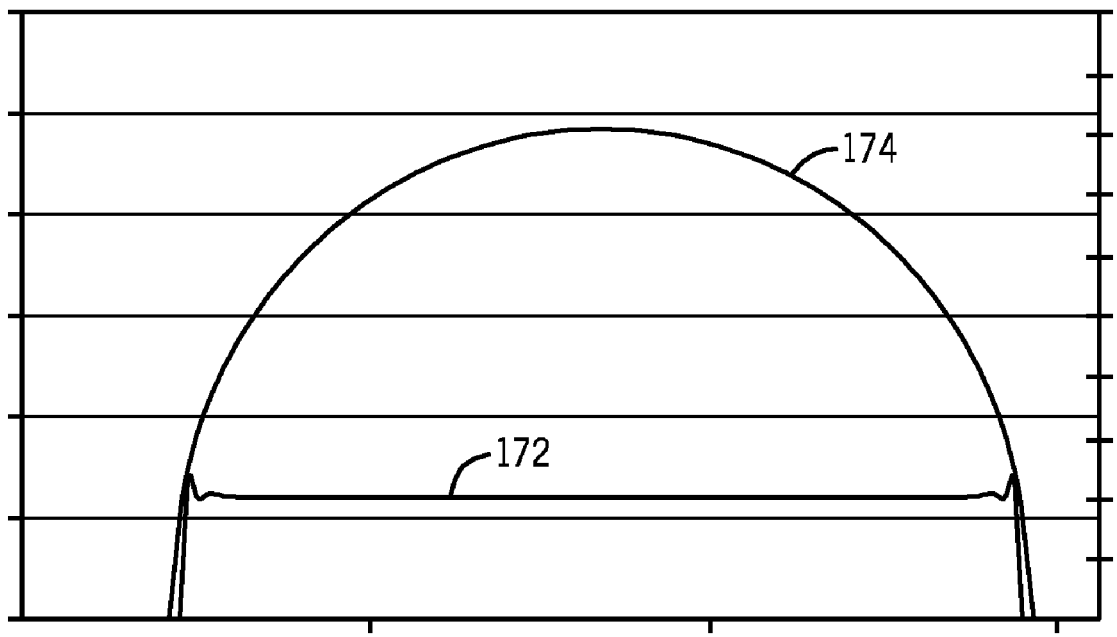
FIG. 16 is a graph illustrating a corrected saturated data profile relative to the unsaturated data profile.

Referring now to FIGS. 15-16, two graphs illustrate an iterative filter technique to determine the effectiveness of a given saturation correction technique in accordance with a further embodiment of the invention. Shown in FIG. 15 are two plots: (1) a plot of saturated CT view data 168 and (2) a plot of filtered data resulting from poor saturation correction of view data 170. As illustrated, when saturation correction is improperly applied, the filtered data 170 exhibits large distortions in the region of the improperly estimated saturated data relative to the unsaturated data. Conversely, as shown in FIG. 16, if saturation correction is properly applied to view data 174, the corrected data yields a "flat" response 172 that is consistent across the filtered view. To measure this "flat" response 172, corrected view data is filtered, but not backprojected and the flatness of the filtered data is determined and used iteratively to provide a better estimate of saturated data correction. That is, before reconstructing an image with saturation corrected data, the above-described filter test may be applied to measure the flatness of the filtered, but not backprojected corrected data. If the filtered data shows distortions such as those illustrated in FIG. 15 then the corrective process was improperly applied. Conversely, if a relatively flat response is measured, the correction technique was well-applied and image quality should be optimized.

Figure 17:
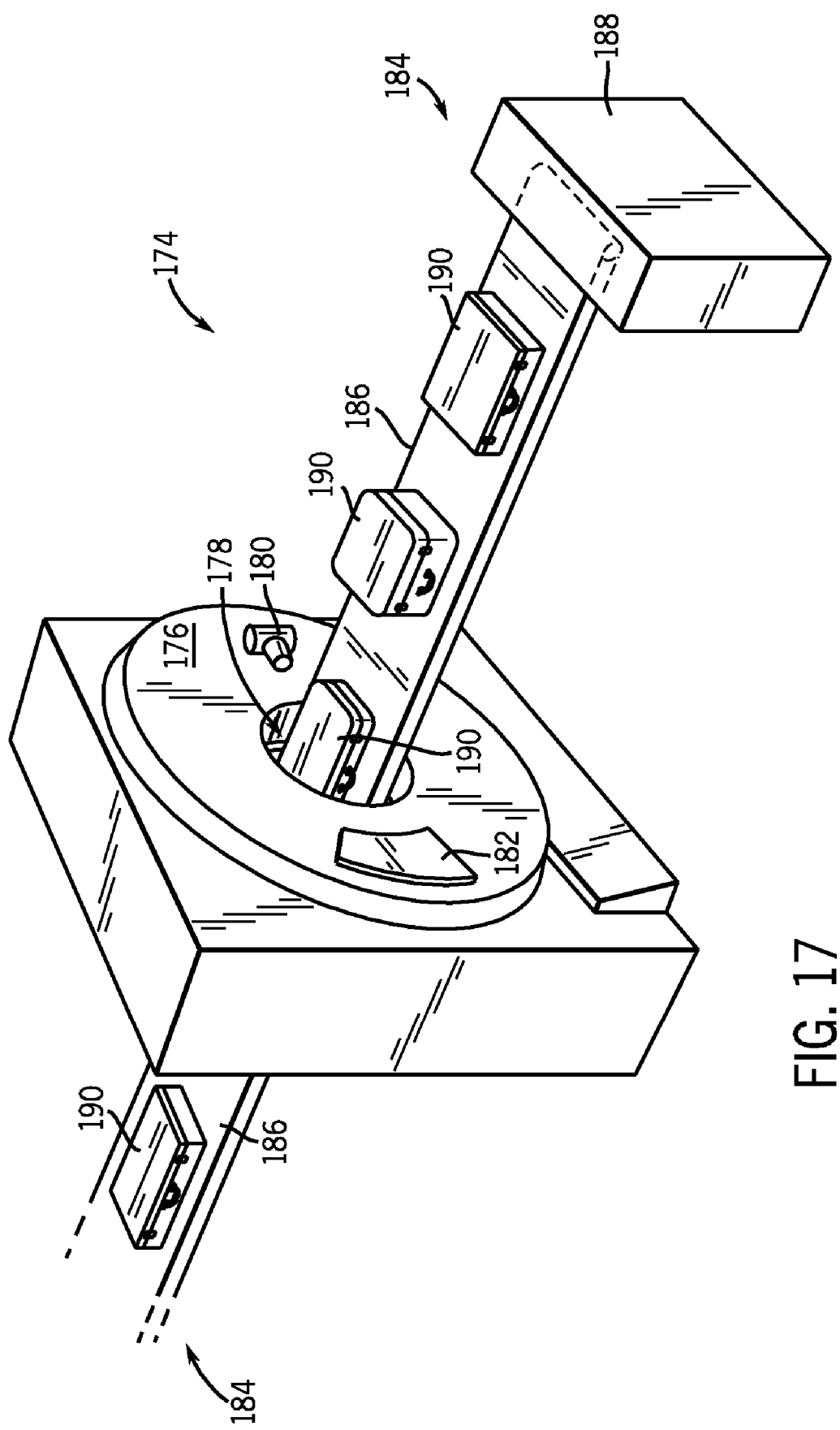
FIG. 17 is a pictorial view of a CT system for use with a non-invasive package inspection system.

Referring now to FIG. 17, package/baggage inspection system 174 includes a rotatable gantry 176 having an opening 178 therein through which packages or pieces of baggage may pass. The rotatable gantry 176 houses a high frequency electromagnetic energy source 180 as well as a detector assembly 182. A conveyor system 184 is also provided and includes a conveyor belt 186 supported by structure 188 to automatically and continuously pass packages or baggage pieces 190 through opening 178 to be scanned. Objects 190 are fed through opening 178 by conveyor belt 186, imaging data is then acquired, and the conveyor belt 186 removes the packages 190 from opening 178 in a controlled and continuous manner. As a result, postal inspectors, baggage handlers, and other security personnel may non-invasively inspect the contents of packages 180 for explosives, knives, guns, contraband, etc.

The saturation correction and verification techniques described above are applicable with conventional as well as multi-energy CT systems, such as those employing limited dynamic range, energy discriminating detectors. The invention is particularly applicable with CT systems having CZT direct-conversion detectors operating in current and/or single photon counting modes. The over-ranging compensation techniques described herein may be utilized to reduce the otherwise stringent dynamic-range requirements of CT detectors. Further, in addition to reducing detector costs, the present invention supports the acquisition of less data (fewer bits/word) thereby positively impacting data communication bandwidths and data storage requirements. The present invention may also be applied to improve extended-view reconstruction commonly encountered with wide-bore CT systems where data extrapolation beyond the limits of the physical detector array may be estimated in similar fashion to the saturated view data estimation techniques.

Therefore, the present invention is directed to a scanner that includes a radiation source and a radiation detector assembly having a plurality of radiation detectors. The scanner also includes a computer operationally connected to the radiation detector assembly and programmed to correct an output of an over-ranging detector with the output of a non-over-ranging detector.

The present invention further discloses a method of CT data correction which method includes acquiring CT data from an object and comparing a profile of the CT data to an off-centered phantom profile. The method further includes correcting saturated portions of the CT data from the off-centered phantom profile. Off-centered phantom profiles used for correction may alternatively be generated using analytic means based on object geometry and predicted material/x-ray interactions to generate synthetic profile data of the required size, geometry and material.

The present invention also includes a CT imaging system and a computer program installed thereon and representing a set of instructions that when executed by a computer causes the computer to correct saturated portions of the CT data from the off-centered phantom profile. Moreover, off-centered phantom profiles used for correction may alternatively be generated using analytic means based on object geometry and predicted material/x-ray interactions to generate synthetic profile data of the required size, geometry and material.

In accordance with another aspect, the present invention includes a computer readable storage medium having a computer program stored thereon and representing a set of instructions that when executed by a computer causes the computer to normalize signal values for each detector element of a CT detector. The computer program further compares a signal value for a detector element to a pair of thresholds, characterizes a CT view corresponding to the signal value of a given detector as one of a normal view, a noisy view, and a saturated view from the comparison, and applies a filter kernel to the CT view if the CT view is characterized as a noisy view. The computer program applies a saturated view correction to the CT view if the CT view is characterized as a saturated view.

The present invention has been described in terms of the preferred embodiment, and it is recognized that equivalents, alternatives, and modifications, aside from those expressly stated, are possible and within the scope of the appending claims.

What is claimed is:

1. A CT imaging system comprising:
   a rotatable gantry having an opening therein to receive a subject to be scanned;
   an x-ray source disposed within the rotatable gantry and configured to project a fan beam of x-rays at the subject during CT data acquisition; and
   a computer programmed to:
   acquire CT data that includes at least normal data and saturated data from a subject;
   compare a profile of the normal data to an off-centered phantom;
   generate data from the off-centered phantom; and
   correct the saturated data using the generated data.

2. The CT imaging system of claim 1 wherein the off-centered phantom profile includes one of an off-centered water and synthetic water data profile.

3. The CT imaging system of claim 1 wherein the off-centered phantom profile includes one of an off-centered cylindrical object and synthetic cylindrical object profile.

4. The CT imaging system of claim 1 wherein the off-centered phantom profile includes one of an off-centered elliptical object and synthetic elliptical object profile.

5. A method of CT data correction comprising the steps of:
   acquiring CT data from an object, the CT data including normal data and saturated data;
   comparing a profile of the normal data to an off-centered phantom or synthetic data profile; and
   correcting for saturation in the data from the comparison.

6. The method of claim 5 further comprising analytically determining a synthetic profile based on the object geometry and material.

7. The method of claim 5 further comprising the steps of:
   approximating an object shape and position; and
   selecting the off-centered phantom profile from a number of off-centered phantom profiles from the object shape and position; or
   generating the off-centered synthetic data profile from the object shape and position.

8. The method of claim 7 further comprising the steps of:
   estimating a line-fit to a last set of non-saturated values of the normal data;
   determining a slope and a line intercept of the line-fit; and
   determining the off-centered phantom or synthetic data profile that should be selected for correcting saturated portions of the CT data from the slope and the line intercept.

9. The method of claim 8 further comprising the step of:
   generating a sinogram from the CT data;
   identifying an edge of the sinogram;
   determining a degree of curvature at the edge of the sinogram; and
   from the degree of curvature, determining a radius of curvature of an edge of the object from which the selected CT data is acquired.

10. The method of claim 9 further comprising the steps of:
    determining an initial curvature at the edge of the sinogram;
    determining a final curvature at the edge of the sinogram;
    determining an average of the initial curvature and the final curvature; and
    determining a radius of curvature of the edge of the sinogram from the average.

11. The method of claim 7 further comprising the steps of determining a radius of curvature of an edge of the object from which the normal data is acquired and, from the radius of curvature, determining an extrapolation radius.

12. The method of claim 11 further comprising the step of selecting the off-centered phantom profile from either one of (A) a number of off-centered phantom profiles or (B) generating the synthetic data profile based on the extrapolation radius.

13. The method of claim 7 further comprising the step of determining a center of mass of the object from scout data acquired from the object.

14. The method of claim 13 further comprising the step of carrying out a lateral scout and an AP scout to acquire object size and position information.

15. The method of claim 5 further comprising the steps of:
identifying noisy data; and
applying a filter kernel to the data to generate non-noisy data.

16. The method of claim 15 wherein the step of applying a filter kernel further comprises the steps of:
setting a strength and a range of the filter kernel based on the signal value of the noisy data; and
replacing the noisy data with view correction data.

17. An imaging system comprising:
a rotatable gantry having an opening therein to receive a subject to be scanned;
an x-ray source disposed within the rotatable gantry and configured to project a fan beam of x-rays at the subject during CT data acquisition; and
a computer programmed to:
acquire CT data from an object;
segregate the acquired CT data for a detector element into normal data and corrupted data;
select the normal data;
compare a profile of the normal data to an off-centered phantom or synthetic data profile; and
use the off-centered phantom or synthetic data profile to correct for saturation.

18. The imaging system of claim 17 wherein the computer is further programmed to analytically determine a synthetic profile based on the object shape and position.

19. The imaging system of claim 17 wherein the computer is further programmed to determine an extrapolation radius from a radius of curvature of the object.

20. The imaging system of claim 19 wherein the synthetic profile includes a profile based on an extrapolation radius of the object.

* * * * *